United States Patent
Taftaf et al.

(10) Patent No.: US 10,059,656 B2
(45) Date of Patent: *Aug. 28, 2018

(54) CATALYST COMPOSITION FOR POLYMERIZATION OF OLEFINS

(71) Applicants: SAUDI BASIC INDUSTRIES CORPORATION, Riyadh (SA); SABIC GLOBAL TECHNOLOGIES B.V., Bergen op Zoom (NL)

(72) Inventors: Mansour I. Taftaf, Peninsula, OH (US); Jaiprakash Brijlal Sainani, Baroda (IN); Vladimir Aleksandrovich Zakharov, Geleen (NL); Gennadii Dimitrievich Bukatov, Geleen (NL); Vimalkumar Mahendrabhai Patel, Bangalore (IN); Sergei Andreevich Sergeev, Geleen (NL); Martin Alexander Zuideveld, Kelmis (BE); Aurora Alexandra Batinas-Geurts, Sittard (NL); Nourdin Ghalit, Amstenrade (NL)

(73) Assignees: SABIC GLOBAL TECHNOLOGIES B.V., Bergen op Zoom (NL); SAUDI BASIC INDUSTRIES CORPORATION, Riyadh (SA)

(*) Notice: Subject to any disclaimer, the term of this patent is extended or adjusted under 35 U.S.C. 154(b) by 0 days.

This patent is subject to a terminal disclaimer.

(21) Appl. No.: 15/104,822

(22) PCT Filed: Dec. 19, 2014

(86) PCT No.: PCT/EP2014/078790
§ 371 (c)(1),
(2) Date: Jun. 15, 2016

(87) PCT Pub. No.: WO2015/091978
PCT Pub. Date: Jun. 25, 2015

(65) Prior Publication Data
US 2016/0340293 A1    Nov. 24, 2016

Related U.S. Application Data

(60) Provisional application No. 61/939,962, filed on Feb. 14, 2014.

(30) Foreign Application Priority Data

Dec. 20, 2013 (EP) .................................. 13199170

(51) Int. Cl.
*C07C 233/69* (2006.01)
*C07C 235/48* (2006.01)
(Continued)

(52) U.S. Cl.
CPC .......... *C07C 233/69* (2013.01); *B01J 31/0202* (2013.01); *C07C 233/18* (2013.01);
(Continued)

(58) Field of Classification Search
None
See application file for complete search history.

(56) References Cited

U.S. PATENT DOCUMENTS 4,384,087 A      5/1983 Capshew
2016/0311946 A1  10/2016 Zuideveld et al.

FOREIGN PATENT DOCUMENTS

EP    1086961 A1    5/2001
EP    1862480 A1    12/2007
(Continued)

OTHER PUBLICATIONS

International Search Report for PCT/EP2014/078798 dated Mar. 12, 2015, 4 pages.
(Continued)

*Primary Examiner* — Catherine S Branch
(74) *Attorney, Agent, or Firm* — Cantor Colburn LLP

(57) ABSTRACT

A catalyst composition including the compound of Formula I as an internal electron donor,

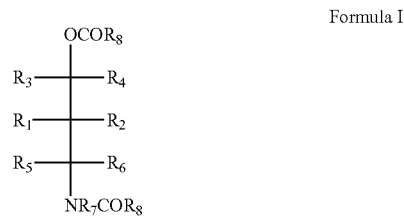

Formula I wherein:

$R_1$, $R_2$, $R_3$, $R_4$, $R_5$ and $R_6$ are independently selected from a group consisting of hydrogen, straight, branched and cyclic alkyl and aromatic substituted and unsubstituted hydrocarbyl having 1 to 20 carbon atoms; $R_7$ is selected from a group consisting of straight, branched and cyclic alkyl and aromatic substituted and unsubstituted hydrocarbyl having 1 to 20 carbon atoms; and $R_8$ is selected from a group consisting of aromatic substituted and unsubstituted hydrocarbyl having 6 to 20 carbon atoms. Also disclosed is a process for preparing said polymerization catalyst composition; a polymerization catalyst system comprising said catalyst composition, a co-catalyst and optionally an external electron donor; a polyolefin obtainable by the process; and use of the compound of Formula I as in internal electron donor in catalysts for polymerization of olefins.

18 Claims, No Drawings

(51) Int. Cl.
*C07C 233/18* (2006.01)
*C08F 110/06* (2006.01)
*B01J 31/02* (2006.01)

(52) U.S. Cl.
CPC .......... *C07C 235/48* (2013.01); *C08F 110/06* (2013.01); *B01J 2231/64* (2013.01); *B01J 2531/007* (2013.01); *C08F 2410/01* (2013.01)

(56) References Cited

FOREIGN PATENT DOCUMENTS

| WO | 9632427 A1 | 10/1996 |
| WO | 2007134851 A1 | 11/2007 |
| WO | 2008-077770 A1 | 7/2008 |
| WO | 2011106494 A1 | 9/2011 |
| WO | 2011106497 A1 | 9/2011 |
| WO | 2011106500 A1 | 9/2011 |
| WO | 2014001257 A1 | 1/2014 |

OTHER PUBLICATIONS

Written Opinion of the International Searching Authority for PCT/EP2014/078798 dated Mar. 12, 2015 6 pages.
International Search Report Authority for PCT/EP2014/078790 dated Mar. 17, 2015, 4 pages.
Pullukat, Thomas and Hoff, Raymond E., "Silica-Based Ziegler-Natta Catalysts: A Patent Review", Catal. Rev, Sci. Eng. 41(3&4), 389-428 (1999).
Written Opinion of the International Searching Authority for PCT/EP2014/078790 dated Mar. 17, 2015, 4 pages.

CATALYST COMPOSITION FOR POLYMERIZATION OF OLEFINS

This application is a national stage application of PCT/EP2014/078790 filed Dec. 19, 2014, which claims priority to U.S. Provisional Application 61/939,962 filed Feb. 14, 2014 and European Application EP13199170.5 filed Dec. 20, 2013, all of which are hereby incorporated by reference in their entirety.

The invention relates to a catalyst composition for polymerization of olefins. The invention also relates to a process for preparing said catalyst composition. Furthermore, the invention is directed to a catalyst system for polymerization of olefins comprising the said catalyst composition, a co-catalyst and optionally an external electron donor; a process of making polyolefins by contacting an olefin with said catalyst system and to polyolefins obtainable by said process. The invention also relates to the use of said catalyst composition in the polymerization of olefins.

Ziegler-Natta catalyst systems and their components are commonly known as being suitable for preparing polyolefins, such as polypropylene. The term Ziegler-Natta is known in the art and typically refers to catalyst systems comprising a transition metal-containing solid catalyst compound; an organo-metal compound and optionally one or more electron donor compounds (external donors). The transition metal-containing solid catalyst compound comprises a transition metal halide of i.e. titanium, chromium, vanadium, supported on a metal or metalloid compound, such as magnesium chloride or silica. An overview of such catalyst types is for example given by T. Pullukat and R. Hoff in Catal. Rev.—Sci. Eng. 41, vol. 3 and 4, 389-438, 1999. It is generally known that for instance i) by varying the transition metal; the type of support; the internal/external donors; and/or the co-catalyst type; ii) by adding additional compounds; and/or iii) by introducing certain components in different process steps of making Ziegler-Natta types of catalysts, the catalyst activity, morphology and the properties of the polyolefins made by using such catalysts, such as molecular weight distribution and isotacticity can be tuned. The molecular weight distribution (MWD) influences the properties of polyolefins and as such influences the end-uses of a polymer; a broad MWD tends to improve the flowability at high shear rate during the processing and the processing of polyolefins in applications requiring fast processing at fairly high die swell, such as in blowing and extrusion techniques.

There is, however, an on-going need in industry for olefin polymerization catalysts showing better performance, especially better control of stereochemistry and allowing preparation of polyolefins having a broader molecular weight distribution.

It is thus an object of the invention to provide a further catalyst composition for the polymerization of olefins. It is a further object of the present invention to provide a catalyst composition which shows better performance, especially shows better control of stereochemistry and allows the preparation of polyolefins having a broader molecular weight distribution.

At least one of the aforementioned objects of the present invention is achieved with a catalyst composition for the polymerization of olefins, which catalyst composition comprises a compound represented by Formula I below as an internal electron donor,

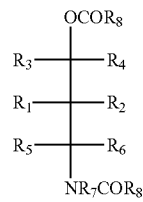

Formula I wherein:
$R_1$, $R_2$, $R_3$, $R_4$, $R_5$ and $R_6$ are the same or different and are independently selected from a group consisting of hydrogen, straight, branched and cyclic alkyl and aromatic, substituted and unsubstituted, hydrocarbyl having 1 to 20 carbon atoms; $R_7$ is selected from a group consisting of straight, branched and cyclic alkyl and aromatic, substituted and unsubstituted, hydrocarbyl having 1 to 20 carbon atoms; and $R_8$ is selected from a group consisting of aromatic substituted and unsubstituted hydrocarbyl having 6 to 20 carbon atoms; N is nitrogen atom; O is oxygen atom; and C is carbon atom.

With aromatic substituted and unsubstituted hydrocarbyl having 6 to 20 carbon atoms is meant either a C6-C20 unsubstituted aromatic hydrocarbyl group or a C6-C20 substituted aromatic hydrocarbyl group.

Preferably, $R_1$, $R_2$, $R_3$, $R_4$, $R_5$ and $R_6$ are independently selected from a group consisting of hydrogen and straight, branched and cyclic alkyl and aromatic substituted and unsubstituted hydrocarbyl 1 to 10 carbon atoms. More preferably, $R_1$, $R_2$, $R_3$, $R_4$, $R_5$ and $R_6$ are independently selected from a group consisting of hydrogen, $C_1$-$C_{10}$ straight and branched alkyl; $C_3$-$C_{10}$ cycloalkyl; $C_6$-$C_{10}$ aryl; and $C_7$-$C_{10}$ alkaryl and aralkyl group. Even more preferably, $R_1$, $R_2$, $R_3$, $R_4$, $R_5$ and $R_6$ are independently selected from a group consisting of hydrogen, methyl, ethyl, propyl, isopropyl, butyl, t-butyl, phenyl, trifluoromethyl and halophenyl group. Most preferably, $R_1$, $R_2$, $R_3$, $R_4$, $R_5$ and $R_6$ are each hydrogen, methyl, ethyl, propyl, t-butyl, phenyl or trifluoromethyl.

Preferably, $R_1$ and $R_2$ are each a hydrogen atom. More preferably, $R_1$ and $R_2$ are each a hydrogen atom and each of $R_3$, $R_4$, $R_5$ and $R_6$ is selected from the group consisting of hydrogen, $C_1$-$C_{10}$ straight and branched alkyls; $C_3$-$C_{10}$ cycloalkyls; $C_6$-$C_{10}$ aryls; and $C_7$-$C_{10}$ alkaryl and aralkyl group; even more preferably, $R_3$, $R_4$, $R_5$ and $R_6$ are each selected from the group consisting of hydrogen, methyl, ethyl, propyl, isopropyl, butyl, t-butyl, phenyl, trifluoromethyl and halophenyl group; most preferably, $R_3$, $R_4$, $R_5$ and $R_6$ are each hydrogen, methyl, ethyl, t-butyl propyl, phenyl or trifluoromethyl.

Preferably, at least one of $R_3$ and $R_4$ and at least one of $R_5$ and $R_6$ is having at least one carbon atom, being selected from the group as defined above. More preferably, when one of $R_3$ and $R_4$ and one of $R_5$ and $R_6$ has at least one carbon atom then the other one of $R_3$ and $R_4$ and of $R_5$ and $R_6$ is each a hydrogen atom. Most preferably, when one of $R_3$ and $R_4$ and one of $R_5$ and $R_6$ has at least one carbon atom, then the other one of $R_3$ and $R_4$ and of $R_5$ and $R_6$ is each a hydrogen atom and $R_1$ and $R_2$ is each a hydrogen atom.

Preferably, $R_7$ is the same or different than any of $R_1$, $R_2$, $R_3$, $R_4$, $R_5$ and $R_6$ with the provision that $R_7$ is not a hydrogen atom.

Preferably, $R_7$ is selected from a group consisting of straight, branched and cyclic alkyl and aromatic substituted and unsubstituted hydrocarbyl having 1 to 10 carbon atoms.

More preferably, $R_7$ is selected from a group consisting of $C_1$-$C_{10}$ straight and branched alkyl; $C_3$-$C_{10}$ cycloalkyl; $C_6$-$C_{10}$ aryl; and $C_7$-$C_{10}$ alkaryl and aralkyl group. Even more preferably, $R_7$ is selected from a group consisting of methyl, ethyl, propyl, isopropyl, butyl, t-butyl, phenyl, benzyl and substituted benzyl and halophenyl group. Most preferably, $R_7$ is methyl, ethyl, propyl, isopropyl, benzyl or phenyl; and even most preferably, $R_7$ is methyl, ethyl or propyl.

$R_8$ can be the same or different than any of $R_1$-$R_7$ and is preferably an aromatic substituted and unsubstituted hydrocarbyl having 6 to 10 carbon atoms. More preferably, $R_8$ is selected from the group consisting of $C_6$-$C_{10}$ aryl unsubstituted or substituted with e.g. an acylhalide or an alkoxyde; and $C_7$-$C_{10}$ alkaryl and aralkyl group; for instance, 4-methoxyphenyl, 4-chlorophenyl, 4-methylphenyl. Particularly preferred, $R_8$ is substituted or unsubstituted phenyl, benzyl, naphthyl, ortho-tolyl, para-tolyl oranisol group. Most preferably, $R_8$ is phenyl.

Preferably, $R_1$ and $R_2$ is each a hydrogen atom and one of $R_3$ and $R_4$ and one of $R_5$ and $R_6$ is selected from the group consisting of $C_1$-$C_{10}$ straight and branched alkyl; $C_3$-$C_{10}$ cycloalkyl; $C_6$-$C_{10}$ aryl; and $C_7$-$C_{10}$ alkaryl and aralkyl group; more preferably $R_5$ and $R_6$ is selected from the group consisting of $C_1$-$C_{10}$ straight alkyl, such as methyl, ethyl, propyl, isopropyl, butyl, t-butyl, phenyl, trifluoromethyl and halophenyl group; and most preferably, one of $R_3$ and $R_4$ and one of $R_5$ and $R_6$ is methyl.

It has been surprisingly found out that the catalyst composition comprising the compound of Formula I as an internal electron donor shows better control of stereochemistry and allows preparation of polyolefins, particularly of polypropylenes having broader molecular weight distribution and higher isotacticity. Polyolefins having broad molecular weight distribution are herein polyolefins that may have a $M_w/M_n$ higher than 6 or than 6.5 or even higher than 7, a broad molecular weight distribution being desirable in the development of different grades of polymer used in certain applications, such as thermoforming, pipes, foams, films, blow-molding. The high isotacticity indicates low amount of amorphous atactic polymer in the products obtained, such as for example lower than 3 wt. %, lower than 2 wt. % or even lower than 1 wt. % of the total amount of polymer. The xylene solubles content of the polyolefins obtained with the catalyst composition according to the present invention is also low, for instance lower than 6 wt. % or lower than 5 wt. %, lower than 4 wt. % and or lower than 3 wt. %. The methods used in the present invention to determine the molecular weight distribution, the amount of atactic polymer, the xylene solubles content and melt flow range are described in the experimental part of the present invention.

A further advantage of the present invention is that low amount of wax is formed, i.e. low molecular weight polymers during the polymerization reaction, which results in reduced or no "stickiness" on the inside walls of the polymerization reactor and inside the reactor. In addition, the catalyst composition according to the present invention can be phthalate-free and thus allows obtaining non-toxic polyolefins showing no harmful effects on human health and which thus can be used for instance in food and medical industry. Furthermore, the low melt flow range values (MFR) of the polymers obtained by using the catalyst compositions according to the present invention, i.e. MFR lower than 6 dg/min, lower than 4 dg/min and even lower than 3 dg/min indicate improved process stability in terms of producing polymers having stable MFR values.

"$M_w$" and "$M_n$" in the context of the present invention means the ratio of the weight average molecular weight $M_w$ and the number average molecular weight $M_n$ of a sample, as measured according to ASTM D6474-12.

"PDI" in the context of the present invention means the ratio of the weight average molecular weight $M_w$ and the number average molecular weight $M_n$ of a sample, as measured according to ASTM D6474-12. As used herein, the terms "PDI" and "polydispersity index" are interchangeable.

"MWD" in the context of the present invention means distribution of the molecular weight of a sample, as represented by the ratio of the weight average molecular weight $M_w$ and the number average molecular weight $M_n$ of a sample as measured according to ASTM D6474-12. As used herein, the terms "MWD" and "molecular weight distribution" are interchangeable.

"average particle size" or "$d_{50}$" in the context of the present invention means the statistical average of the particle size distribution as measured according to ISO 13320:2009, in which the average particle size is expressed by $x_{50}$ or $d_{50}$.

"span value" in the context of the present invention represents an indicator for the width of the particle size distribution as measured according to ISO 13320:2009. The span value is calculated according to the formula:

$$\text{Span Value} = \frac{d_{90} - d_{10}}{d_{50}}$$

In which $d_{90}$ is equal to $x_{90}$ as defined in ISO 13320:2009, $d_{10}$ is equal to $x_{10}$ as defined in ISO 13320:2009, and $d_{50}$ is equal to $x_{50}$ as defined in ISO 13320:2009.

"APP" as used in the context of present invention means atactic polypropylene. The weight percentage of APP as used in the context of the present invention means the percentage of polypropylene of the total quantity of polypropylene produced in a slurry polymerization process that is retained in the solvent, especially for example hexane, that is used in said slurry polymerization process. The weight percentage of APP may be determined according to the following procedure: a quantity A of the product stream from said slurry polymerization process is collected. This quantity A is filtered using a filter having pores between 10 and 16 μm in diameter, to obtain a filtrate Y and a polymer quantity of weight x, said polymer quantity of weight x being the quantity of material that remained on the filter. Said filtrate Y is dried over a steam bath and then under vacuum at 60° C. to obtain a dry mass of APP of weight z. The weight percentage of APP is calculated by:

$$APP(\text{in wt \%}) = \frac{z}{z+x} * 100\%$$

"MFR" in the context of the present invention means the melt mass-flow rate as measured according to ISO 1133:2005, at 230° C. under a load of 2.16 kg. As used herein, the terms "MFR", "melt flow rate" and "melt mass-flow rate" are interchangeable.

"XS" in the context of the present invention means the xylene soluble fraction in terms of percentage of polymer that does not precipitate out upon cooling of a polymer solution in xylene, said polymer solution having been subjected to reflux conditions, down from the reflux temperature, which equals the boiling temperature of xylene, to 25°

C. XS is measured according to ASTM D5492-10. As used herein, the terms "XS" and "xylene soluble fraction" are interchangeable.

An internal donor (also referred to as internal electron donor) is herein defined as an electron-donating compound that is commonly described in prior art as a reactant in the preparation of a solid catalyst component for a Ziegler-Natta catalyst system for olefins polymerization; i.e. contacting a magnesium-containing support with a halogen-containing Ti compound and an internal donor.

As used herein, the term "hydrocarbyl" is a substituent containing only hydrogen or carbon atoms, including linear or branched, saturated or unsaturated aliphatic radical, such as alkyl, alkenyl, and alkynyl; alicyclic radical, such as cycloalkyl, cycloalkenyl; aromatic radical, such as monocyclic or polycyclic aromatic radical, as well as combinations thereof, such as alkaryl and aralkyl.

As described therein, the term "substituted hydrocarbyl" is a hydrocarbyl group that is substituted with one or more non-hydrocarbyl substituent groups. A non-limiting example of a non-hydrocarbyl substituent is a heteroatom. As used herein, a hydrocarbon is an atom other than carbon or hydrogen. Non-limiting examples of heteroatoms include: halogens (F, Cl, Br, I), N, O, P, B, S and Si.

Preferably, the catalyst composition according to the invention comprises the compound having Formula I as the only internal electron donor in a Ziegler-Natta catalyst composition.

Without being limited thereto, particular examples of the compounds of Formula I are the structures as depicted in formulas (II)-(XII). For instance, the structure in Formula (II) may correspond to 4-[benzoyl(methyl)amino]pentan-2-yl benzoate; Formula (III) to 3-[benzoyl(cyclohexyl)amino]-1-phenylbutyl benzoate; Formula (IV) to 3-[benzoyl(propan-2-yl)amino]-1-phenylbutyl benzoate; Formula (V) to 4-[benzoyl(propan-2-yl)amino]pentan-2-yl benzoate; Formula (VI) to 4-[benzoyl(methyl)amino]-1,1,1-trifluoropentan-2-yl benzoate; Formula (VII) to 3-(methylamino)-1,3-diphenylpropan-1-oldibenzoate; Formula (VIII) to 2,2,6,6-tetramethyl-5-(methylamino)heptan-3-ol dibenzoate; Formula (IX) to 4-[benzoyl (ethyl)amino]pentan-2-yl benzoate; Formula (X) to 3-(methyl)amino-propan-1-ol dibenzoate; Formula (XI) to 3-(methyl)amino-2,2-dimethylpropan-1-ol dibenzoate; Formula (XII) to 4-(methylamino) pentan-2-yl bis (4-methoxy)benzoate). The compounds of formula (II), (IX), (XII) and (VIII) are the most preferred internal electron donors in the catalyst composition according to the present invention as they allow preparation of polyolefins having broader molecular weight distribution and higher isotacticity. The low melt flow range values (MFR) of the polymers obtained by using the catalyst compositions according to the present invention, i.e. MFR lower than 6 dg/min, lower than 4 dg/min and even lower than 3 dg/min indicate improved process stability in terms of producing polymers having stable MFR values.

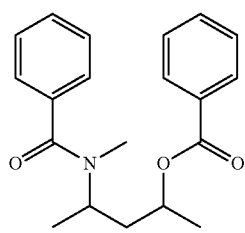

Formula (II)

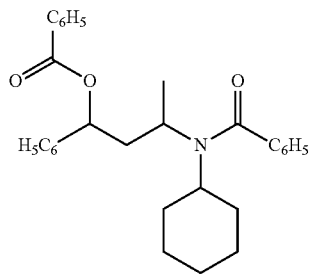

Formula (III)

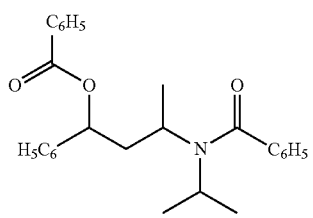

Formula (IV)

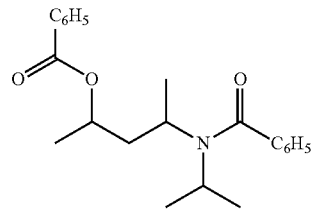

Formula (V)

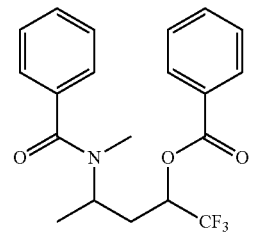

Formula (VI)

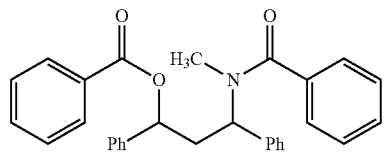

Formula (VII)

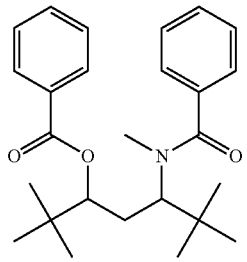

Formula (VIII)

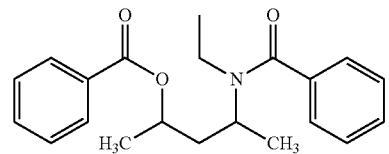

Formula (IX)

Formula (X)

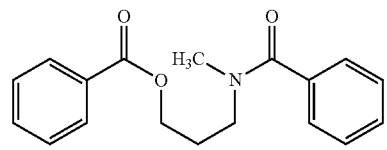

Formula (XI)

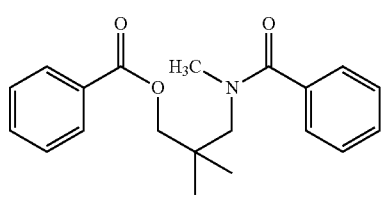

Formula (XII)

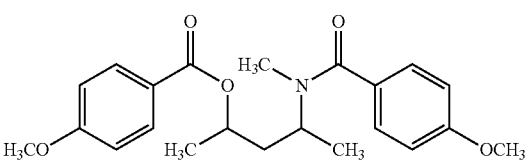

The present invention also relates to a novel compound being selected from the group consisting of 4-[benzoyl (methyl)amino]pentan-2-yl benzoate (Formula II), 3-[benzoyl(cyclohexyl)amino]-1-phenylbutyl benzoate (Formula III); 3-[benzoyl(propan-2-yl)amino]-1-phenylbutyl benzoate (Formula IV); 4-[benzoyl(propan-2-yl)amino]pentan-2-yl benzoate (Formula V); 4-[benzoyl(methyl)amino]-1,1,1-trifluoropentan-2-yl benzoate (Formula VI); 3-(methylamino)-1,3-diphenylpropan-1-ol dibenzoate (Formula VII); 2,2,6,6-tetramethyl-5-(methylamino)heptan-3-ol dibenzoate (Formula VIII); 4-(ethyl)aminopentan-2-yl dibenzoate (Formula IX); 3-(methyl)amino-propan-1-ol dibenzoate (Formula X); 3-(methyl)amino-2,2-dimethylpropan-1-ol dibenzoate (Formula XI); 4-(methylamino)pentan-2-yl bis (4-methoxy)benzoate) (Formula XII). Each of these compounds can be used as an internal electron donor in a Ziegler-Natta catalyst composition, giving result to polyolefins having broader molecular weight distribution and high isotacticity, as shown in the examples of the present patent application. The low melt flow range values (MFR) of the polymers obtained by using the catalyst compositions according to the present invention, i.e. MFR lower than 6 dg/min, lower than 4 dg/min and even lower than 3 dg/min indicate improved process stability in terms of producing polymers having stable MFR values.

The compound according to Formula I can be made by any method known in the art. In this respect, reference is made to J. Chem. Soc. Perkin trans. 11994, 537-543 and to Org. Synth. 1967, 47, 44. These documents disclose a step a) of contacting a substituted 2,4-diketone with a substituted amine in the presence of a solvent to give a β-enaminoketone; followed by a step b) of contacting the β-enaminoketone with a reducing agent in the presence of a solvent to give a γ-aminoalcohol. The substituted 2,4-diketone and the substituted amine can be applied in step a) in amounts ranging from 0.5 to 2.0 mole, preferably from 1.0 to 1.2 mole. The solvent in steps a) and b) may be added in an amount of 5 to 15 volume, based on the total amount of the diketone, preferably of 3 to 6 volume. The β-enaminoketone to diketone mole ratio in step b) may be of from 0.5 to 6, preferably from 1 to 3. The reducing agent to β-enaminoketone mole ratio in step b) may be of from 3 to 8, preferably from 4 to 6; the reducing agent may be selected from the group comprising metallic sodium, NaBH$_4$ in acetic acid, Ni—Al alloy. Preferably, the reducing agent is metallic sodium because it is a cheap reagent.

The γ-aminoalcohol that can be used for making compound (I) can be synthesized as described in the literature and also mentioned herein above or this compound can be directly purchased commercially and used as a starting compound in a reaction to obtain the compound represented by Formula I. Particularly, the γ-aminoalcohol can be reacted with a substituted or unsubstituted benzoyl chloride in the presence of a base to obtain the compound represented by Formula ((referred herein also as step c), regardless that γ-aminoalcohol was synthesized as described in the literature or commercially purchased). The molar ratio between the substituted or unsubstituted benzoyl chloride and the γ-aminoalcohol may range from 2 to 4, preferably from 2 to 3. The base may be any basic chemical compound that is able to deprotonate the γ-aminoalcohol. Said base can have a pK$_a$ of at least 5; or at least 10 or preferably between 5 and 40, wherein pK$_a$ is a constant already known to the skilled person as the negative logarithm of the acid dissociation constant k$_a$. Preferably, the base is pyridine; a trialkyl amine, e.g. triethylamine; or a metal hydroxide e.g. NaOH, KOH. Preferably, the base is pyridine. The molar ratio between the base and the γ-aminoalcohol may range from 3 to 10, preferably from 4 to 6.

The solvent used in any of steps a), b) and c) can be selected from any organic solvents, such as toluene, dichloromethane, 2-propanol, cyclohexane or mixtures of any organic solvents. Preferably, toluene is used in each of steps a), b) and c). More preferably, a mixture of toluene and 2-propanol is used in step b). The solvent in step c) can be added in an amount of 3 to 15 volume, preferably from 5 to 10 volume based on the γ-aminoalcohol.

The reaction mixture in any of steps a), b) and c) may be stirred by using any type of conventional agitators for more than about 1 hour, preferably for more than about 3 hours and most preferably for more than about 10 hours, but less than about 24 hours. The reaction temperature in any of steps a) and b) may be the room temperature, i.e. of from about 15 to about 30° C., preferably of from about 20 to about 25° C. The reaction temperature in step c) may range between 0 and 10° C., preferably between 5 and 10° C. The reaction mixture in any of steps a), b) and c) may be refluxed for more than about 10 hours, preferably for more than about 20 hours but less than about 40 hours or until the reaction is complete (reaction completion may be measured by Gas Chromatography, GC). The reaction mixture of steps a) and b) may be then allowed to cool to room temperature, i.e. at a temperature of from about 15 to about 30° C., preferably of from about 20 to about 25° C. The solvent and any excess of components may be removed in any of steps a), b) and c) by any method known in the art, such as evaporation, washing. The obtained product in any of steps b) and c) can be separated from the reaction mixture by any method known in the art, such as by extraction over metal salts, e.g. sodium sulfate.

The molar ratio of the internal donor of Formula I relative to the magnesium can be from 0.02 to 0.5. Preferably, this molar ratio is between 0.05 and 0.2.

The process for preparing the catalyst composition according to the present invention comprises contacting a magnesium-containing support with a halogen-containing titanium compound and an internal donor, wherein the internal electron donor is the compound represented by Formula I.

The magnesium-containing support and halogen-containing titanium compounds used in the process according to the present invention are known in the art as typical components of a Ziegler-Natta catalyst composition. Any of said Ziegler-Natta catalyst components known in the art can be used in the process according to the present invention. For instance, synthesis of such titanium-magnesium based catalyst compositions with different magnesium-containing support-precursors, such as magnesium halides, magnesium alkyls and magnesium aryls, and also magnesium alkoxy and magnesium aryloxy compounds for polyolefin production, particularly of polypropylenes production are described for instance in U.S. Pat. No. 4,978,648, WO96/32427A1, WO01/23441 A1, EP1283 222A1, EP1222 214B1; U.S. Pat. No. 5,077,357; U.S. Pat. No. 5,556,820; U.S. Pat. No. 4,414,132; U.S. Pat. No. 5,106,806 and U.S. Pat. No. 5,077,357 but the present process is not limited to the disclosure in these documents.

Preferably, the process for preparing the catalyst composition according to the present invention comprises the steps of:

i) contacting a compound $R^9_z MgX_{2-z}$ wherein $R^9$ is aromatic, aliphatic or cyclo-aliphatic group containing 1 to 20 carbon atoms, X is a halide, and z is in a range of larger than 0 and smaller than 2, with an alkoxy- or aryloxy-containing silane compound to give a first intermediate reaction product;

ii) contacting the solid $Mg(OR^1)_x X_{2-x}$ with at least one activating compound selected from the group formed by electron donors and compounds of formula $M(OR^{10})_{v-w}(OR^{11})_w$, wherein M is Ti, Zr, Hf, Al or Si and $M(OR^{10})_{v-w}(R^{11})_w$, wherein M is Si, each $R^{10}$ and $R^{11}$, independently, represent an alkyl, alkenyl or aryl group, v is the valency of M, v being either 3 or 4 and w is smaller than v; and iii) contacting the second intermediate reaction product with a halogen-containing Ti-compound, an internal electron donor represented by Formula I,

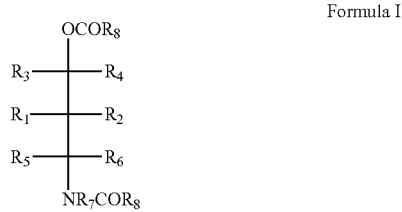

Formula I wherein:
$R_1$, $R_2$, $R_3$, $R_4$, $R_5$ and $R_6$ are the same or different and are independently selected from a group consisting of hydrogen, straight, branched and cyclic alkyl and aromatic substituted and unsubstituted hydrocarbyl having 1 to 20 carbon atoms; $R_7$ is selected from a group consisting of straight, branched and cyclic alkyl and aromatic substituted and unsubstituted hydrocarbyl having 1 to 20 carbon atoms; and
$R_8$ is selected from a group consisting of aromatic substituted and unsubstituted hydrocarbyl having 6 to 20 carbon atoms; N is nitrogen atom; O is oxygen atom; and C is carbon atom.

In an embodiment, the process for preparing the catalyst composition according to the present invention comprises the steps of:

i) contacting a compound $R^9_z MgX_{2-z}$ wherein $R^9$ is aromatic, aliphatic or cyclo-aliphatic group containing 1 to 20 carbon atoms, X is a halide, and z is in a range of larger than 0 and smaller than 2, with an alkoxy- or aryloxy-containing silane compound to give a first intermediate reaction product;

ii) contacting the solid $Mg(OR^1)_x X_{2-x}$ with at least one activating compound selected from the group formed by compounds of formula $M(OR^{10})_{v-w}(OR^{11})_w$, wherein M is Si, each $R^{10}$ and $R^{11}$, independently, represent an alkyl, alkenyl or aryl group, v is the valency of M, v being either 3 or 4 and w is smaller than v; and iii) contacting the second intermediate reaction product with a halogen-containing Ti-compound, an internal electron donor represented by the Formula I,

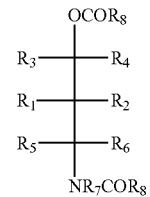

Formula I wherein:
$R_1$, $R_2$, $R_3$, $R_4$, $R_5$ and $R_6$ are the same or different and are independently selected from a group consisting of hydrogen, straight, branched and cyclic alkyl and aromatic substituted and unsubstituted hydrocarbyl having 1 to 20 carbon atoms; $R_7$ is selected from a group consisting of straight, branched and cyclic alkyl and aromatic substituted and unsubstituted hydrocarbyl having 1 to 20 carbon atoms; and
$R_8$ is selected from a group consisting of aromatic substituted and unsubstituted hydrocarbyl having 6 to 20 carbon atoms; N is nitrogen atom; O is oxygen atom; and C is carbon atom.

This process according to the present invention results in catalyst compositions, which allow obtaining polyolefins, preferably polypropylene having broader molecular weight distribution and high isotacticity.

Step i)

In step i) a first intermediate reaction product, i.e. a solid magnesium-containing support is prepared by contacting a compound or a mixture of compounds of formula $R^9_z MgX_{2-z}$ wherein $R^9$ is aromatic, aliphatic or cyclo-aliphatic group containing 1 to 20 carbon atom, X is a halide, and z is larger than 0 and smaller than 2, with an alkoxy- or aryloxy-containing silane compound, as for example described in WO 96/32427 A1 and WO01/23441 A1. In the compound $R^9_z MgX_{2-z}$, also referred to as Grignard compound, X is preferably chlorine or bromine, more preferably chlorine.

$R^9$ can be an alkyl, aryl, aralkyl, alkoxide, phenoxide, etc., or mixtures thereof. Suitable examples of group $R^9$ are methyl, ethyl, n-propyl, i-propyl, n-butyl, i-butyl, t-butyl, hexyl, cyclohexyl, octyl, phenyl, tolyl, xylyl, mesityl and benzyl. In a preferred embodiment of the invention, $R^9$ represents an aromatic group, for instance a phenyl group.

Preferably, as Grignard compound $R^4_z MgX^4_{2-z}$ used in step i) a phenyl Grignard or a butyl Grignard is used. The selection for either the phenyl Grignard or the butyl Grignard depends on the requirements.

When Grignard compound is used, a compound according to the formula $R^4_z MgX^4_{2-z}$ is meant. When phenyl Grignard is used a compound according to the formula $R^4_z MgX^4_{2-z}$ wherein $R^4$ is phenyl, e.g. PhMgCl, is meant. When butyl Grignard is used, a compound according to the formula $R^4{}_zMgX^4{}_{2-z}$ wherein $R^4$ is butyl, e.g. BuMgCl or n-BuMgCl, is meant.

An advantage of the use of phenyl Grignard are that it is more active that butyl Grignard. Preferably, when butyl Grignard is used, an activation step using an aliphatic alcohol, such as methanol is carried out in order to increase the activity. Such an activation step may not be required with the use of phenyl Grignard. A disadvantage of the use of phenyl Grignard is that benzene rest products may be present and that it is more expensive and hence commercially less interesting.

An advantage of the use of butyl Grignard is that it is benzene free and is commercially more interesting due to the lower price. A disadvantage of the use of butyl Grignard is that in order to have a high activity, an activation step is required.

The process to prepare the procatalyst according to the present invention can be carried out using any Grignard compound, but the two stated above are the two that are most preferred.

The Grignard compound of formula $R^9{}_zMgX_{2-z}$, wherein z is larger than 0 and smaller than 2, is preferably characterized by z being from about 0.5 to 1.5.

The alkoxy- or aryloxy-containing silane used in step i) is typically a compound or a mixture of compounds with the general formula $Si(OR^{13})_{4-n}R^{14}{}_n$, wherein n can range from 0 up to 3, preferably n is from 0 up to and including 1, and wherein each $R^{13}$ and $R^{14}$ groups, independently, represent an alkyl, alkenyl or aryl group, optionally containing one or more hetero atoms for instance O, N, S or P, with, for instance, 1-20 C-atoms. Examples of suitable silane-compounds include tetramethoxysilane, tetraethoxysilane, methyltrimethoxysilane, methyltributoxysilane, phenyltriethoxysilane. Preferably, tetraethoxysilane is used as silane-compound in preparing the solid Mg-containing compound in the process according to the invention.

Preferably, in step i) the silane-compound and the Grignard compound are introduced simultaneously to a mixing device to result in particles of advantageous morphology, especially of the larger particles, as described in WO 01/23441 A1. Here, 'morphology' does not only refer to the shape of the particles of the solid Mg-compound and the catalyst made therefrom, but also to the particle size distribution (also characterized as span), its fines content, powder flowability, and the bulk density (viz. the weight per unit volume of a material, including voids inherent in the material as tested; measured as apparent density according to ASTM D1895-96 Reapproved 2010-e1, test method A) of the catalyst particles. Moreover, it is well known that a polyolefin powder produced in polymerization process using a catalyst system based on such catalyst component has a similar morphology as the catalyst component (the so-called "replica effect"; see for instance S. van der Ven, Polypropylene and other Polyolefins, Elsevier 1990, p. 8-10). Accordingly, almost round polymer particles are obtained with a length/diameter ratio (l/D) smaller than 2 and with good powder flowability. Introduced simultaneously means that the introduction of the Grignard compound and the silane-compound is done in such way that the molar ratio Mg/Si does not substantially vary during the introduction of these compounds to the mixing device, as described in WO 01/23441 A1. The silane-compound and Grignard compound can be continuously or batch-wise introduced to the mixing device. Preferably, the both compounds are introduced continuously to a mixing device.

It is explicitly noted that it is possible that the Grignard compound in step i) may alternatively have a different structure, for example, may be a complex. Such complexes are already known to the skilled person in the art; a particular example of such complexes is $Phenyl_4Mg_3Cl_2$.

The mixing device can have various forms; it can be a mixing device in which the silane-compound is premixed with the Grignard compound, the mixing device can also be a stirred reactor, in which the reaction between the compounds takes place. Preferably, the compounds are premixed before the mixture is introduced to the reactor for step i). In this way, a catalyst component is formed with a morphology that leads to polymer particles with the best morphology (high bulk density, narrow particle size distribution, (virtually) no fines, excellent flowability). The Si/Mg molar ratio during step i) may vary within wide limits for instance from 0.2 to 20. Preferably, the Si/Mg molar ratio is from 0.4 to 1.0.

The period of premixing in above indicated reaction step may vary between wide limits, for instance 0.1 to 300 seconds. Preferably premixing is performed during 1 to 50 seconds.

The temperature during the premixing step is not specifically critical, and may for instance range between 0 and 80° C.; preferably the temperature is between 10° C. and 50° C. The reaction between said compounds may, for instance, take place at a temperature between −20° C. and 100° C.; preferably at a temperature of from 0° C. to 80° C.

The first intermediate reaction product obtained from the reaction between the silane compound and the Grignard compound is usually purified by rinsing with an inert solvent, for instance a hydrocarbon solvent with for example 1-20 C-atoms, like pentane, iso-pentane, hexane or heptane. The solid product can be stored and further used as a suspension in said inert solvent. Alternatively, the product may be dried, preferably partly dried, and preferably under mild conditions; e.g. at ambient temperature and pressure.

The first intermediate reaction product obtained by this step i) may comprise a compound of the formula $Mg(OR^9)_xX_{2-x}$, wherein the group $R^9$ is an alkyl or an aryl group containing 1-12 carbon atoms, although the present invention is not limited thereby. X is a halide, and x is larger than 0 and smaller than 2, preferably between 0.5 and 1.5. Preferably, X is chlorine or bromine and more preferably, X is chlorine.

In cases where the first intermediate reaction product is represented by $Mg(OR^9)_xX_{2-x}$, and $R^9$ is alkyl, the alkyl group may be linear or branched. Preferably, the $R^9$ group contains 1-8 carbon atoms. More preferably, at least one of the $R^9$-groups represents an ethyl group. In a preferred embodiment, each $R^9$-group represents an ethyl group.

$R^9{}_zMgX_{2-z}$ used in step i) may be prepared by contacting metallic magnesium with an organic halide $R^9X$, as described in WO 96/32427 A1 and WO01/23441 A1. All forms of metallic magnesium may be used, but preferably use is made of finely divided metallic magnesium, for example magnesium powder. To obtain a fast reaction it is preferable to heat the magnesium under nitrogen prior to use. $R^9$ and X have the same meaning as described above. Combinations of two or more organic halides $R^9X$ can also be used.

The magnesium and the organic halide $R^9X$ can be reacted with each other without the use of a separate dispersant; the organic halide $R^9X$ is then used in excess. The organic halide $R^9X$ and the magnesium can also be brought into contact with one another and an inert dispersant. Examples of these dispersants are: aliphatic, alicyclic or aromatic dispersants containing from 4 up to 20 carbon atoms.

Preferably, in this step of preparing $R^9_z MgX_{2-z}$, also an ether is added to the reaction mixture. Examples of ethers are: diethyl ether, diisopropyl ether, dibutyl ether, diisobutyl ether, diisoamyl ether, diallyl ether, tetrahydrofuran and anisole. Dibutyl ether and/or diisoamyl ether are preferably used. Preferably, an excess of chlorobenzene is used as the organic halide $R^9X$. Thus, the chlorobenzene serves as dispersant as well as organic halide $R^9X$.

The organic halide/ether ratio acts upon the activity of the catalyst component. The chlorobenzene/dibutyl ether volume ratio may for example vary between 75:25 and 35:65, preferably between 70:30 and 50:50.

Small amounts of iodine and/or alkyl halides can be added to cause the reaction between the metallic magnesium and the organic halide $R^9X$ to proceed at a higher rate. Examples of alkyl halides are butyl chloride, butyl bromide and 1,2-dibromoethane. When the organic halide $R^9X$ is an alkyl halide, iodine and 1,2-dibromoethane are preferably used.

The reaction temperature for preparing $R^9_z MgX_{2-z}$ normally is between 20 and 150° C.; the reaction time is normally between 0.5 and 20 hours. After the reaction for preparing $R^9_z MgX_{2-z}$ is completed, the dissolved reaction product may be separated from the solid residual products.

Step ii)

The electron donors and the compounds of formula $M(OR^{10})_{v-w}(OR^{11})_w$ and $M(OR^{10})_{v-w}(R^{11})_w$ may be also referred herewith as activating compounds.

Examples of suitable electron donors that can be used in step ii) are known to the skilled person and include alcohols, carboxylic acids and carboxylic acid derivatives. Preferably, an alcohol is used as the electron donor in step ii). More preferably, the alcohol is a linear or branched aliphatic or aromatic having 1-12 carbon atoms. Even more preferably, the alcohol is selected from methanol, ethanol, butanol, isobutanol, hexanol, xylenol and benzyl alcohol. Most preferably, the alcohol is ethanol or methanol.

Examples of suitable carboxylic acids include formic acid, acetic acid, propionic acid, butyric acid, isobutanoic acid, acrylic acid, methacrylic acid, maleic acid, fumaric acid, tartaric acid, cyclohexanoic monocarboxylic acid, cis-1,2-cyclohexanoic dicarboxylic acid, phenylcarboxylic acid, toluene carboxylic acid, naphthalene carboxylic acid, phthalic acid, isophthalic acid, terephthalic acid and/or trimellitic acid.

$R^{10}$ and $R^{11}$ groups can be a linear, branched or cyclic alkyl or alkenyl group, suitable groups containing from 1 to 20 carbon atoms, preferably 1-12 or 1-8 carbon atoms. The groups may differ independently or be the same. Preferably, at least one of the $R^{10}$ groups represents an ethyl group. In preferred embodiments, $R^{10}$ and $R^{11}$ are ethyl, propyl or butyl; more preferably, all groups are ethyl groups. $R^{10}$ and $R^{11}$ can also be aromatic hydrocarbon groups, optionally substituted with e.g. alkyl groups and can contain for example from 6 to 20 carbon atoms.

Preferably, M in said activating compound is Ti or Si. Preferably, the value of w is 0, the activating compound being for example a titanium tetraalkoxide containing 4-32 C-atoms. The four alkoxide groups in the compound may be the same or may differ independently. Preferably, at least one of the alkoxy groups in the compound is an ethoxy group. More preferably the compound is a tetraalkoxide, like titanium tetraethoxide. Si-containing compounds suitable as activating compounds are the same as listed above for step i).

Preferably, a Ti-based compound, for example titanium tetraethoxide, is used together with an alcohol, like ethanol or methanol in step ii) to give the solid catalyst support.

If two or more compounds are used in step ii) of the preferred process according to the invention, their order of addition is not critical, but may affect catalyst performance depending on the compounds used. A skilled person may optimize their addition based on some experiments. The compounds of step ii) can be added together or sequentially.

The first intermediate reaction product can be contacted in any sequence with the activating compounds. In one preferred embodiment, the electron donor is first added to the first intermediate reaction product and then the compound $M(OR^{10})_{v-w}(OR^{11})_w$ or $M(OR^{10})_{v-w}(R^{11})_w$ is added; in this order no agglomeration of solid particles is observed. The compounds in step ii) are preferably added slowly, for instance during a period of 0.1-6, preferably during 0.5-4 hours, most preferably during 1-2.5 hours, each.

The inert dispersant is preferably a hydrocarbon solvent. The dispersant may be for example an aliphatic or aromatic hydrocarbon with 1-20 C-atoms. Preferably, the dispersant is an aliphatic hydrocarbon, more preferably pentane, isopentane, hexane or heptane, heptane being most preferred. In the preferred process according to the invention the molar ratio of activating compound to the magnesium atom of the first intermediate reaction product may range between wide limits and is, for instance, between 0.02 and 1.0. Preferably, the molar ratio is between 0.1 and 0.7, depending on the type of activating compound. In the process according to the invention the temperature in step ii) can be in the range from −20° C. to 70° C., preferably from −10° C. to 50° C., more preferably in the range between 0° C. and 30° C. Preferably, at least one of the reaction components is dosed in time, for instance during 0.1 to 6, preferably during 0.5 to 4 hours, more particularly during 1-2.5 hours.

The obtained second intermediate reaction product may be a solid and may be further washed, preferably with the solvent also used as inert dispersant; and then stored and further used as a suspension in said inert solvent. Alternatively, the product may be dried, preferably partly dried, preferably slowly and under mild conditions; e.g. at ambient temperature and pressure.

Starting from a solid Mg-containing product of controlled morphology, said morphology is not negatively affected during treatment with the activating compound. The solid second intermediate reaction product obtained is considered to be an adduct of the Mg-containing compound and the at least one compound as defined in step ii), and is still of controlled morphology. This second intermediate reaction product being a solid catalyst support containing magnesium is subsequently contacted in step iii) with a halogen-containing titanium compound and an internal electron donor compound having Formula I.

Preferably, the solid first intermediate reaction product is contacted with an alcohol and then with a titanium tetraalkoxide and an inert dispersant to give a solid second intermediate reaction product, which second intermediate reaction product is then contacted in step iii) with titanium tetrachloride and an internal donor represented by Formula I.

Step iii)

The Ti/Mg molar ratio in the reaction between the second intermediate reaction product and halogen-containing titanium compound preferably is between 10 and 100, most preferably, between 10 and 50.

The molar ratio of the internal electron donor of Formula I relative to the magnesium may vary between wide limits, for instance between 0.02 and 0.5. Preferably, this molar ratio is between 0.05 and 0.4; more preferably between 0.1 and 0.3; and most preferably between 0.1 and 0.2.

Preferably, during contacting the second intermediate reaction product and the halogen-containing titanium compound an inert dispersant is used. The dispersant preferably is chosen such that virtually all side products formed are dissolved in the dispersant. Suitable dispersants include for example aliphatic and aromatic hydrocarbons and halogenated aromatic solvents with for instance 4-20 C-atoms. Examples include toluene, xylene, benzene, decane, o-chlorotoluene and chlorobenzene.

The reaction temperature during contacting in step iii) the second intermediate reaction product and the halogen-containing titanium compound is preferably between 0° C. and 150° C., more preferably between 50° C. and 150° C., and more preferably between 100° C. and 140° C. Most preferably, the reaction temperature is between 110° C. and 125° C. The obtained reaction product may be washed, usually with an inert aliphatic or aromatic hydrocarbon or halogenated aromatic compound, to obtain the catalyst component of the invention. If desired the reaction and subsequent purification steps may be repeated one or more times. A final washing is preferably performed with an aliphatic hydrocarbon to result in a suspended or at least partly dried catalyst component, as described above for the other steps.

The invention further relates to a catalyst composition for polymerization of olefins obtainable by the process according to the invention.

The invention also relates to a polymerization catalyst system that comprises the catalyst composition according to the invention and a co-catalyst. Preferably, the catalyst system also comprises an external electron-donating compound, also referred to as external electron donor, or simply external donor. The main function of this external donor compound is to affect the stereoselectivity of the catalyst system in polymerization of olefins having 3 or more carbon atoms, and therefore it may be also referred to as selectivity control agent. Preferably, the co-catalyst is an organometallic compound containing a metal from group 1, 2, 12 or 13 of the Periodic System of the Elements (Handbook of Chemistry and Physics, 70th Edition, CRC Press, 1989-1990), wherein the system further comprises an external electron donor.

The invention further relates to a process of making a polyolefin by contacting at least one olefin with a polymerization catalyst system comprising the catalyst composition according to the present invention. Preferably, the polyolefin made by using the catalyst system of the present invention is a polypropylene. It is an advantage of the present invention that polyolefins obtainable by employing said catalyst has a broad molecular weight distribution and a low amount of atactic fraction and xylene solubles.

The preparation of polyolefins may take place by polymerizing one or more olefins simultaneously and/or successively in the presence of a catalyst system comprising the catalyst according to the invention, a co-catalyst and optionally an external donor. The olefin according to the invention may be selected from mono- and di-olefins containing from 2 to 10 carbon atoms, such as for example ethylene, propylene, butylene, hexene, octene and/or butadiene.

According to a preferred embodiment of the invention the olefin is propylene or a mixture of propylene and ethylene, to result in a propylene homopolymer or copolymer. A propylene copolymer is herein meant to include both so-called random copolymers with relatively low comonomer content, e.g. up to 10 mol %, as well as so-called impact copolymers comprising higher comonomer contents, e.g. from 5 to 80 mol %, more typically from 10 to 60 mol %. The impact copolymers are actually blends of different propylene polymers; such copolymers can be made in one or two reactors and can be blends of a first component of low comonomer content and high crystallinity, and a second component of high comonomer content having low crystallinity or even rubbery properties. Such random and impact copolymers are well-known to the skilled in the art.

Generally, the co-catalyst is an organometallic compound containing a metal from group 1, 2, 12 or 13 of the Periodic System of the Elements (Handbook of Chemistry and Physics, 70th Edition, CRC Press, 1989-1990). Preferably, the co-catalyst is an organoaluminum compound. The organoaluminum compound may be, for instance, a compound having the formula $AlR^{15}_3$, wherein each $R^{15}$ independently represents an alkyl group with, for instance, 1-10 C-atoms or an aryl group with, for instance, 6-20 C-atoms. Examples of a suitable organoaluminum compound are trimethylaluminum, triethylaluminum, triisobutylaluminum, and/or trioctylaluminum. Preferably, the co-catalyst is triethylaluminum.

Examples of suitable external donors include organosilicon compounds. Mixtures of external donors can also be used. Examples of organo-silicon compounds that are suitable as external donor are compounds or mixtures of compounds of general formula $Si(OR^{16})_{4-n}R^{17}_n$, wherein n can be from 0 up to 2 preferably n is 1 or 2 as higher values have no positive effect on stereospecificity, and each $R^{16}$ and $R^{17}$, independently, represents an alkyl or aryl group, optionally containing one or more hetero atoms for instance O, N, S or P, with, for instance, 1-20 C-atoms, as defined above for $R^{13}$ and $R^{14}$. Examples of suitable compounds include the silane-compounds that can be used at step i), as described above. Preferably, the organo-silicon compound used as external donor is n-propyl trimethoxysilane. The molar ratio of the metal of the co-catalyst relative to titanium in the polymerization catalyst system during the polymerization may vary for instance from 5 to 2000. Preferably, this ratio is between 50 and 300.

The aluminum/external donor molar ratio in the polymerization catalyst system preferably is between 0.1 and 200; more preferably between 1 and 100.

The polymerization process can be carried out in the gas phase or in the liquid phase (in bulk or slurry). In the case of polymerization in a slurry (liquid phase) a dispersing agent is present. Suitable dispersing agents include for example n-butane, isobutane, n-pentane, isopentane, hexane, heptane, octane, cyclohexane, benzene, toluene, xylene and liquid propylene. The polymerization conditions of the process according to the invention, such as the polymerization temperature and time, monomer pressure, avoidance of contamination of catalyst, choice of polymerization medium in slurry processes, the use of further ingredients (like hydrogen) to control polymer molar mass, and other conditions are well known to persons of skill in the art. The polymerization temperature may vary within wide limits and is, for example for propylene polymerization between 0° C. and 120° C., preferably between 40° C. and 100° C. The pressure during (propylene) (co)polymerization is for instance between 0.1 and 6 MPa, preferably between 0.5-3 MPa.

The molar mass of the polyolefin obtained during the polymerization can be controlled by adding during the polymerization hydrogen or any other agent known to be suitable for the purpose. The polymerization can be carried out in a continuous mode or batch-wise. Slurry-, bulk-, and gas-phase polymerization processes, multistage processes of each of these types of polymerization processes, or combinations of the different types of polymerization processes in a multistage process are contemplated herein. Preferably, the polymerization process is a single stage gas phase process or a multistage, for instance a 2-stage, gas phase process wherein in each stage a gas-phase process is used.

Examples of gas-phase polymerization processes include both stirred bed reactors and fluidized bed reactor systems; such processes are well known in the art. Typical gas phase α-olefin polymerization reactor systems comprise a reactor vessel to which alpha-olefin monomer(s) and a catalyst system can be added and which contain an agitated bed of growing polymer particles.

The present invention also relates to a polyolefin, preferably a polypropylene obtained or obtainable by a process, comprising contacting an olefin, preferably propylene or a mixture of propylene and ethylene with the catalyst composition according to the present invention. The terms polypropylene and propylene-based polymer are used herein interchangeable. The polypropylene may be a propylene homopolymer or a mixture of propylene and ethylene, such as a propylene-based copolymer, e.g. heterophasic propylene-olefin copolymer; random propylene-olefin copolymer, preferably the olefin in the propylene-based copolymers being ethylene. Such propylene-based (co)polymers are known to the skilled person in the art; they are also described herein above.

The polyolefin, preferably the polypropylene according to the present invention has a molecular weight distribution higher than 6, preferably higher than 7, more preferably higher than 7.5 and for instance below 10 or below 9. The molecular weight distribution of the polyolefins, preferably polypropylene according to the present invention is for instance between 6 and 9, preferably between 6 and 8, more preferably between 7 and 8.

The polyolefin, preferably the polypropylene according to the present invention has a xylene amount of lower than 6 wt. %, preferably lower than 5 wt. %, more preferably lower than 3 wt. % and most preferably lower than 2.7 wt. %. The polyolefin, preferably the polypropylene according to the present invention has a xylene amount of between 2 and 6 wt. %, preferably between 2 and 5 wt. %, more preferably between 2 and 4 wt. % and most preferably, between 2 and 3 wt.

The polyolefin, preferably the polypropylene according to the present invention may further comprise additives, such as nucleating agents, clarifiers, stabilizers, release agents, pigments, dyes, plasticizers, anti-oxidants, antistatics, scratch resistance agents, high performance fillers, impact modifiers, flame retardants, blowing agents, recycling additives, coupling agents, anti microbials, anti-fogging additives, slip additives, anti-blocking additives, polymer processing aids such as lubricants and the like, etc., surface tension modifiers, co-agents, for example 1,4-butanediol dimethacrylate, acrylate or methacrylate; components that enhance interfacial bonding between the polymer and the talc, for example maleated polypropylene etc. Such additives are well known in the art. The skilled person can readily select any suitable combination of additives and additive amounts without undue experimentation. The amount of additives depends on their type and function. Typically, the amount of additives is from 0 to 30 wt. %, for example from 0 to 20 wt. %, for example from 0 to 10 wt. % or from 0 to 5 wt. % based on the total polymer composition. The sum of all components added in a process to form the polyolefins, preferably the propylene-base polymers or compositions thereof, should add up to 100 wt. %.

The invention also relates to the use of the polyolefins, preferably the polypropylene according to the invention in injection molding, blow molding, extrusion molding, compression molding, thin-walled injection molding, etc., for example in food contact applications.

The polyolefin, preferably the polypropylene according to the present invention may be transformed into shaped (semi)-finished articles using a variety of processing techniques. Examples of suitable processing techniques include injection molding, injection compression molding, thin wall injection molding, extrusion, and extrusion compression molding. Injection molding is widely used to produce articles such as for example caps and closures, batteries, pails, containers, automotive exterior parts like bumpers, automotive interior parts like instrument panels, or automotive parts under the bonnet. Extrusion is for example widely used to produce articles, such as rods, sheets, films and pipes. Thin wall injection molding may for example be used to make thin wall packaging.

Furthermore, the invention relates to a shaped article comprising the polyolefins, preferably the polypropylene according to the present invention.

The present invention further relates to the use of the compound according to Formula I as an internal electron donor in a catalyst composition for polymerization of olefins. Polyolefins with improved properties, e.g. having broad molecular weight distribution and high isotacticity are produced with using the compound of Formula I as internal electron donor in a Ziegler-Natta catalyst composition.

It is noted that the invention relates to all possible combinations of features recited in the claims. Features described in the description may further be combined.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention will be further elucidated with the following examples without being limited hereto.

EXAMPLES

Preparation of 4-[benzoyl(methyl)amino]pentan-yl benzoate (AB)

Step a)

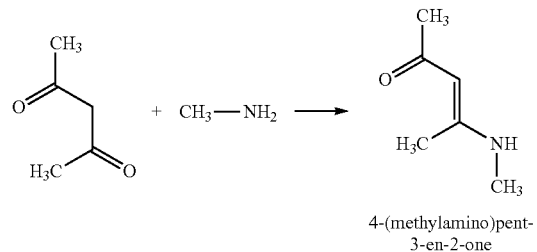

4-(methylamino)pent-3-en-2-one

40% monomethylamine solution in water (48.5 g, 0.625 mol) was added drop wise to a stirred solution of substituted pentane-2,4-dione (50 g, 0.5 mol) in toluene (150 ml. After the addition, the reaction mass was stirred at room temperature for 3 hours and then refluxed. During the reflux the water formed was azeotropically removed using a Dean-stark trap. Then the solvent was removed under reduced pressure to give 4-(methylamino)pent-3-en-2-one, 53.5 g, which was then directly used for reduction.

Step b)

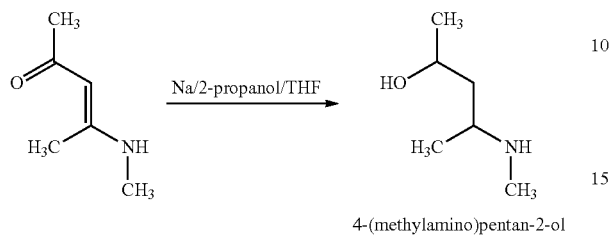

4-(methylamino)pentan-2-ol 4-(methylamino)-pent-3-en-2-one (100 g) was added to a stirred mixture of 1000 ml 2-propanol and 300 ml toluene. To this solution, small piece of metallic sodium 132 g was gradually added at a temperature of between 25-60° C. The reaction mass was refluxed for 18 h. The mass was cooled to room temperature and was poured in cold water and extracted with dichloromethane. The extract was dried over sodium sulfate, filtered and then evaporated under reduced pressure to give 65 g 4-(methylamino)pentan-2-ol (isomer mixture)oil.

Step c)

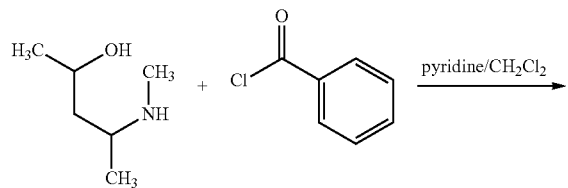

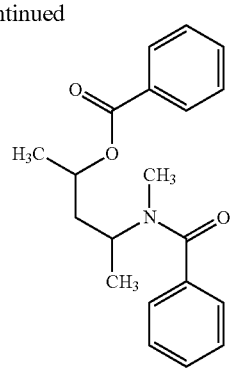

4-[benzoyl(methyl)amino]pentan-2-yl benzoate 4-(methylamino)pentan-2-ol (10 g) was added to a mixture of pyridine (16.8 g) and toluene (100 ml). The mass was cooled to 10° C. and benzoyl chloride (24 g) was added dropwise. The mixture was refluxed for 6 h. The mixture was then diluted with toluene and water. The organic layer was washed with diluted HCl, water saturated bicarbonate and brine solution. The organic layer was dried over sodium sulfate, filtered and then evaporated under reduced pressure. The residue was purified by flash chromatography to form 25 g product as thick oil. The product was characterized by $^1$H NMR and $^{13}$C NMR: m/z=326.4 (m+1), $^1$H NMR (300 MHz, CDCl$_3$) δ=7.95-7.91 (m, 1H), 7.66-7.60 (m, 2H), 7.40-7.03 (m, 5H), 6.78-6.76 (m, 2H), 4.74-5.06 (br m, 1H), 3.91-3.82 (m, 1H), 2.83-2.56 (ddd, 3H), 2.02-1.51 (m, 1H), 1.34-1.25 (dd, 1H), 1.13-1.02 (m, 6H); $^{13}$C NMR (75 MHz, CDCl$_3$), δ=170.9, 170.4, 170.3, 164.9, 164.6, 135.9, 135.8, 135.2, 131.8, 131.7, 131.6, 129.6, 129.4, 129.3, 128.9, 128.4, 128.3, 128.2, 128.0, 127.7, 127.3, 127.2, 127.1, 127.0, 125.7, 125.6, 125.0, 124.9, 68.3, 67.5, 67.3, 49.8, 49.4, 44.9, 44.4, 39.7, 39.0, 38.4, 38.3, 30.5, 29.8, 25.5, 25.1, 19.33, 19.1, 18.9, 18.3, 17.0, 16.8, 16.7.

By applying the same method of preparation, internal electron donors as described and characterized in Table 1 were also obtained:

TABLE 1

| Compound | Structure |
|---|---|
| 4-[ethyl(phenylcarbonyl)amino]pentan-2-yl benzoate (AB-Et):<br>m/z = 339 (m + 1), $^1$H NMR (300MHz, CDCl$_3$) δ = 1-2(m, 9H), 2-2.6(m 4H), 4-4.2 (m, 1H), 5-5.4(m, 1H), 7-8.2(m, 10H), $^{13}$C NMR (75 MHz, CDCl$_3$), δ = 17.5, 19, 20, 36, 42, 52, 70, 126-140, 166, 172. | |
| 2,2,6,6-tetramethyl-5-(N-methylbenzamido)heptan-3-yl-benzoate (AB-TMH):<br>m/z = 409, $^1$H NMR (300MHz, CDCl$_3$) δ = 0.94 (d, 2H), 1.2 (d, 9H), 2.6(s, 3H), 4.8(d, 1H), 4.9(d, 1H), 5.1(t, 2H), 7.2-8.2(10H). $^{13}$C NMR (75 MHz, CDCl$_3$), δ = 26-28, 34, 38, 60, 81, 126-138, 166, 174. | |
| 4-(4-methoxy-N-methylbenzamido)pentane-2-yl-4-methoxy benzoate (AB-p-OMePh)<br>m/z = 385, $^1$H NMR (300MHz, CDCl$_3$) δ = 1.1-1.3(m, 6H), 1.8-1.9(t, 2H), 3.4(s, 3H), 3.8(s, 6H), 4(m, 1H), 4.6(m, 1H), 6.4-7.8(m, 8H). $^{13}$C NMR (75 MHz, CDCl$_3$), δ = 18-22, 28, 32, 40, 46, 52, 56-58, 68, 114, 123, 128-130, 132, 160, 164, 166, 172. | |

Example 1

Preparation of the Catalyst Composition

A. Grignard Formation Step (Step A)

This step was carried out as described in Example XVI of EP 1 222 214 B1. This Example is incorporated by reference.

A stainless steel reactor of 9 l volume was filled with magnesium powder 360 g. The reactor was brought under nitrogen. The magnesium was heated at 80° C. for 1 hour, after which a mixture of dibutyl ether (1 liter) and chlorobenzene (200 ml) was added. Then iodine (0.5 g) and n-chlorobutane (50 ml) were successively added to the reaction mixture. After the color of the iodine had disappeared, the temperature was raised to 94° C. Then a mixture of dibutyl ether (1.6 liter) and chlorobenzene (400 ml) was slowly added for 1 hour, and then 4 liter of chlorobenzene was slowly added for 2.0 hours. The temperature of reaction mixture was kept in interval 98-105° C. The reaction mixture was stirred for another 6 hours at 97-102° C. Then the stirring and heating were stopped and the solid material was allowed to settle for 48 hours. By decanting the solution above the precipitate, a solution of phenylmagnesiumchloride reaction product A with a concentration of 1.3 mol Mg/l has been obtained. This solution was used in the further catalyst preparation.

B. Preparation of the First Intermediate Reaction Product (Step B)

This step was carried out as described in Example XX of EP 1 222 214 B1 (this Example is incorporated by reference), except that the dosing temperature of the reactor was 35° C., the dosing time was 360 min and the propeller stirrer was used. 250 ml of dibutyl ether was introduced to a 1 liter reactor. The reactor was fitted by propeller stirrer and two baffles. The reactor was thermostated at 35° C. The solution of reaction product of step A (360 ml, 0.468 mol Mg) and 180 ml of a solution of 55 ml of tetraethoxysilane (TES) in 125 ml of dibutyl ether (DBE), were cooled to 10° C., and then were dosed simultaneously to a mixing device of 0.45 ml volume supplied with a stirrer and jacket. Dosing time was 360 min. Thereafter the premixed reaction product A and the TES-solution were introduced to a reactor. The mixing device (mini-mixer) was cooled to 10° C. by means of cold water circulating in the mini-mixer's jacket. The stirring speed in the mini-mixer was 1000 rpm. The stirring speed in reactor was 350 rpm at the beginning of dosing and was gradually increased up to 600 rpm at the end of dosing stage. On the dosing completion the reaction mixture was heated up to 60° C. and kept at this temperature for 1 hour. Then the stirring was stopped and the solid substance was allowed to settle. The supernatant was removed by decanting. The solid substance was washed three times using 500 ml of heptane. As a result, a pale yellow solid substance, reaction product B (the solid first intermediate reaction product; the support), was obtained, suspended in 200 ml of heptane. The average particle size of support was 22 µm and span value $(d_{90}-d_{10})/d_{50}=0.5$.

C. Preparation of the Second Intermediate Reaction Product (Step C)

Support activation was carried out as described in Example IV of WO/2007/134851 to obtain the second intermediate reaction product. This Example is incorporated by reference.

In inert nitrogen atmosphere at 20° C. a 250 ml glass flask equipped with a mechanical agitator is filled with slurry of 5 g of reaction product of step B dispersed in 60 ml of heptane. Subsequently a solution of 0.22 ml ethanol (EtOH/Mg=0.1) in 20 ml heptane is dosed under stirring during 1 hour. After keeping the reaction mixture at 20° C. for 30 minutes, a solution of 0.79 ml titanium tetraethoxide (TET/Mg=0.1) in 20 ml of heptane was added for 1 hour. The slurry was slowly allowed to warm up to 30° C. for 90 min and kept at that temperature for another 2 hours. Finally the supernatant liquid is decanted from the solid reaction product (the second intermediate reaction product; activated support) which was washed once with 90 ml of heptane at 30° C.

D. Preparation of the Catalyst Component (Step D)

A reactor was brought under nitrogen and 125 ml of titanium tetrachloride was added to it. The reactor was heated to 100° C. and a suspension, containing about 5.5 g of activated support (step C) in 15 ml of heptane, was added to it under stirring. Then the temperature of reaction mixture was increased to 110° C. for 10 min and 1.92 g of 4-[benzoyl(methyl)amino]pentan-2-yl benzoate (aminobenzoate, AB, AB/Mg molar ratio=0.15) in 3 ml of chlorobenzene was added to reactor and the reaction mixture was kept at 115° C. for 105 min. Then the stirring was stopped and the solid substance was allowed to settle. The supernatant was removed by decanting, after which the solid product was washed with chlorobenzene (125 ml) at 100° C. for 20 min. Then the washing solution was removed by decanting, after which a mixture of titanium tetrachloride (62.5 ml) and chlorobenzene (62.5 ml) was added. The reaction mixture was kept at 115° C. for 30 min, after which the solid substance was allowed to settle. The supernatant was removed by decanting, and the last treatment was repeated once again. The solid substance obtained was washed five times using 150 ml of heptane at 60° C., after which the catalyst component, suspended in heptane, was obtained.

Polymerization of Propylene

Polymerization of propylene was carried out in a stainless steel reactor (with a volume of 0.7 l) in heptane (300 ml) at a temperature of 70° C., total pressure 0.7 MPa and hydrogen presence (55 ml) for 1 hour in the presence of a catalyst system comprising the catalyst component according to step D, triethylaluminum (TEAL) as co-catalyst and n-propyltrimethoxysilane (nPTMS) as external donor. The concentration of the catalyst component was 0.033 g/l; the concentration of TEAL was 4.0 mmol/l; the concentration of nPTMS was 0.2 mmol/l. Data on the catalyst performance for the propylene polymerization is presented in Table 2.

Example 2

Example 2 was carried out in the same way as Example 1, but 4-[benzoyl(ethyl)amino]pentan-2-yl benzoate (formula IX, AB-Et, AB-Et/Mg molar ratio=0.15) in step D was used instead of AB.

Example 3

Example 3-1 was carried out in the same way as Example 1, but 4-(methylamino)-pentane-2-ol di(4-methoxybenzoate) (formula XII, AB-p-MeOPh, AB-p-MeOPh/Mg molar ratio=0.15) in step D was used instead of AB.

Example 4

Example 4 was carried out in the same way as Example 1, but 2,2,6,6-tetramethyl-5-(methyl)amino]heptan-3-ol dibenzoate (formula VIII, AB-TMH, AB-TMH/Mg molar ratio=0.15) in step D was used instead of AB.

Example 5

Example 5 was carried out in the same way as Example 1, but 5 g of Mg(OEt)$_2$ (Aldrich grade) as the Mg-containing support and 2.15 g of AB (AB/Mg molar ratio=0.15) were used in step D.

Example 6

Example 6 was carried out in the same way as Example 1, but 5 g of the Mg-containing support prepared according to U.S. Pat. No. 5,077,357 (production method incorporated by reference) and 1.43 g of AB (AB/Mg molar ratio=0.15) were used in step D.

Example CE1 (Comparative Example 1)

Example CE1 was carried out in the same way as Example 1, but di-n-butylphthalate (DBP)(DBP/Mg molar ratio=0.15) was used instead of AB.

Example CE2 (Comparative Example 2)

Example CE2 was carried out in the same way as Example 1, but 4-[benzoylamino]pentan-2-yl benzoate as described in WO2011106494A1 (incorporated by reference) (AB-H, AB-H/Mg molar ratio=0.15) was used instead of AB.

Example CE3 (Comparative Example 3)

Example CE3 was carried out in the same way as Example 5, but 4-[benzoylamino]pentan-2-yl benzoate (AB-H, AB-H/Mg molar ratio=0.15) was used instead of AB.

TABLE 2

| Ex. | ID type (formula) | ID, wt. % | Ti, wt. % | PP yield, kg/g cat. | APP, wt. % | XS, % | MFR, dg/min | Mw/Mn |
|---|---|---|---|---|---|---|---|---|
| 1 | AB (II) | 17.9 | 2.4 | 4.4 | 0.9 | 2.5 | 0.6 | 7.7 |
| 2 | AB-Et (IX) | 15.6 | 3.0 | 4.8 | 1.7 | 3.6 | 1.0 | 7.4 |
| 3 | AB-p-OMePh (XII) | 10.8 | 3.2 | 4.7 | 1.6 | 4.1 | 2.4 | 6.2 |
| 4 | AB-TMH (VIII) | 7.0 | 2.9 | 5.6 | 1.1 | 5.6 | 5.7 | 7.1 |
| 5 | AB (II) | 19.8 | 4.5 | 5.5 | 1.4 | 2.7 | 0.9 | 7.8 |
| 6 | AB (II) | 20.4 | 4.3 | 6.3 | 0.9 | 2.5 | 1.1 | 7.5 |
| CE1 | DBP | 10.5 | 2.6 | 13.5 | 0.4 | 2.7 | 12.7 | 4.8 |
| CE2 | AB-H[1)] | 10.0 | 2.6 | 5.5 | 0.7 | 3.5 | 4.6 | 6.5 |
| CE3 | AB-H[1)] | 10.3 | 2.9 | 5.7 | 0.9 | 3.6 | 4.2 | 6.4 |

[1)]N—H group instead of N—Me group in AB.

The Examples show that a novel catalyst composition for polymerization of olefins was obtained and that said catalyst composition shows better performance, especially shows better control of stereochemistry and allows preparation of polyolefins having a broader molecular weight distribution. For instance, it can be seen that catalyst compositions according to the present invention allow obtaining polypropylene with broader MWD (Ex. 1-6) compared to usual catalyst with phthalate as ID (Ex. CE1). Also, the catalysts having the internal donors comprising the N-Me bond (Ex. 1 and 4-6) or N-Et bond (Ex. 2) show broader MWD (Mw/Mn=7.1-7.8) compared to catalysts with the similar known internal donor having N—H bond (Ex. CE2 and CE3, Mw/Mn=6.4-6.5). At the same time polymers obtained show high isotacticity (XS=2.5-3.6% (Ex. 1, 2, 5 and 6) compared to XS=3.5-3.6% (Ex. CE2 and CE3). It can be noted also that similar good performance of the catalysts comprising the internal donor of Formula I is observed for different magnesium-containing support-precursors (Ex. 1, 5 and 6).

Abbreviations and measuring methods:
PP yield, kg/g cat is the amount of polypropylene obtained per gram of catalyst component.
The $^1$H-NMR and $^{13}$C-NMR spectra were recorded on a Varian Mercury-300 MHz NMR Spectrometer, using deuterated chloroform as a solvent.

The invention claimed is:
1. A catalyst composition for the polymerization of olefins, which catalyst composition comprises the compound represented by Formula I as an internal electron donor,

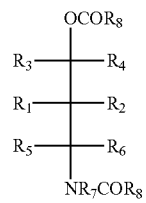

Formula I wherein:
$R_1$, $R_2$, $R_3$, $R_4$, $R_5$ and $R_6$ are the same or different and are independently selected from the group consisting of hydrogen, straight, branched and cyclic alkyl and aromatic substituted and unsubstituted hydrocarbyl having 1 to 20 carbon atoms;
$R_7$ is selected from the group consisting of straight, branched and cyclic alkyl and aromatic substituted and unsubstituted hydrocarbyl having 1 to 20 carbon atoms; and
$R_8$ is selected from the group consisting of aromatic substituted and unsubstituted hydrocarbyl having 6 to 20 carbon atoms;
N is nitrogen atom; O is oxygen atom; and C is carbon atom.
2. The catalyst composition according to claim 1, wherein $R_1$, $R_2$, $R_3$, $R_4$, $R_5$ and $R_6$ are independently selected from the group consisting of hydrogen, $C_1$-$C_{10}$ straight and branched alkyl; $C_3$-$C_{10}$ cycloalkyl; $C_6$-$C_{10}$ aryl; and $C_7$-$C_{10}$ alkaryl and aralkyl groups.

3. The catalyst composition according to claim 1, wherein $R_1$ and $R_2$ are each a hydrogen atom and $R_3$, $R_4$, $R_5$ and $R_6$ are independently selected from the group consisting of $C_1$-$C_{10}$ straight and branched alkyl; $C_3$-$C_{10}$ cycloalkyl; $C_6$-$C_{10}$ aryl; and $C_7$-$C_{10}$ alkaryl and aralkyl groups.

4. The catalyst composition according to claim 1, wherein when one of $R_3$ and $R_4$ and one of $R_5$ and $R_6$ has at least one carbon atom, then the other one of $R_3$ and $R_4$ and of $R_5$ and $R_6$ is each a hydrogen atom.

5. The catalyst composition according to claim 1, wherein $R_7$ is selected from the group consisting of methyl, ethyl, propyl, isopropyl, butyl, t-butyl, phenyl, benzyl, substituted benzyl and halophenyl groups.

6. The catalyst composition according to claim 1, wherein $R_8$ is selected from the group consisting of $C_6$-$C_{10}$ aryl; and $C_7$-$C_{10}$ alkaryl and aralkyl groups.

7. The catalyst composition according claim 1, wherein the internal electron donor is selected from the group consisting of 4-[benzoyl(methyl)amino]pentan-2-yl benzoate; 2,2,6,6-tetramethyl-5-(methylamino)heptan-3-ol dibenzoate; 4-[benzoyl (ethyl)amino]pentan-2-yl benzoate and 4-(methylamino)pentan-2-yl bis (4-methoxy)benzoate).

8. A process for preparing the catalyst composition according to claim 1, comprising contacting a magnesium-containing support with a halogen-containing titanium compound and an internal electron donor according to Formula I.

9. The process according to claim 8, which comprises:
i) contacting a compound $R^9{}_zMgX_{2-z}$ wherein $R^9$ is aromatic, aliphatic or cyclo-aliphatic group containing 1 to 20 carbon atoms, X is a halide, and z is in a range of larger than 0 and smaller than 2, with an alkoxy- or aryloxy-containing silane compound to give a first intermediate reaction product, which is a compound $Mg(OR^1)_xX_{2-x}$ in a solid form, wherein x is in a range of larger than 0 and smaller than 2;
ii) contacting the compound $Mg(OR^1)_xX_{2-x}$ in a solid form with at least one activating compound selected from the group consisting of electron donors and compounds of formula $M(OR^{10})_{v-w}(OR^{11})_w$, wherein M is Ti, Zr, Hf, Al or Si and $M(OR^{10})_{v-w}(R^{11})_w$, wherein M is Si, each $R^{10}$ and $R^{11}$, independently, represent an alkyl, alkenyl or aryl group, v is the valency of M, v being either 3 or 4 and w is smaller than v to give a second intermediate reaction product; and
iii) contacting the second intermediate reaction product with a halogen-containing Ti-compound, an internal electron donor represented by Formula I,

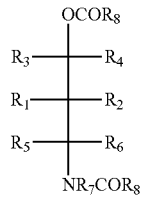

Formula I wherein:
$R_1$, $R_2$, $R_3$, $R_4$, $R_5$ and $R_6$ are the same or different and are independently selected from the group consisting of hydrogen, straight, branched and cyclic alkyl and aromatic substituted and unsubstituted hydrocarbyl having 1 to 20 carbon atoms;

$R_7$ is selected from the group consisting of straight, branched and cyclic alkyl and aromatic substituted and unsubstituted hydrocarbyl having 1 to 20 carbon atoms; and $R_8$ is selected from the group consisting of aromatic substituted and unsubstituted hydrocarbyl having 6 to 20 carbon atoms;

N is nitrogen atom; O is oxygen atom; and C is carbon atom.

10. A catalyst composition obtained by the process according to claim 8.

11. A polymerization catalyst system comprising the catalyst composition according to claim 1, a co-catalyst and optionally an external electron donor.

12. A process of making a polyolefin, comprising contacting an olefin with the catalyst system according to claim 11.

13. The catalyst composition according to claim 3, wherein $R_3$, $R_4$, $R_5$ and $R_6$ are independently selected from $C_1$-$C_{10}$ straight and branched alkyl and phenyl.

14. The catalyst composition according to claim 6, wherein $R_8$ is selected from the group consisting of substituted or unsubstituted phenyl, benzyl, naphthyl, ortho-tolyl, para-tolyl or anisol groups.

15. The process according to claim 9, wherein the first intermediate reaction product is contacted with an alcohol and a titanium tetraalkoxide in step ii).

16. A polymerization catalyst system comprising the catalyst composition according to claim 7, a co-catalyst and optionally an external electron donor.

17. The catalyst composition according to claim 10, wherein
$R_1$ and $R_2$ are each a hydrogen atom;
$R_3$, $R_4$, $R_5$ and $R_6$ are selected from the group consisting of methyl, ethyl, propyl, isopropyl, butyl, t-butyl, or phenyl groups;
$R_7$ is selected from the group consisting of methyl, ethyl, propyl, isopropyl, butyl, t-butyl, phenyl, benzyl, substituted benzyl and halophenyl groups; and
$R_8$ is phenyl.

18. A polymerization catalyst system comprising the catalyst composition according to claim 17, a co-catalyst and optionally an external electron donor.

* * * * *